United States Patent [19]

Casali et al.

[11] Patent Number: 5,131,411
[45] Date of Patent: Jul. 21, 1992

[54] CUSTOM-FITTING EARPLUG FORMED IN SITU USING FOAMING ACTION

[75] Inventors: John G. Casali, Blacksburg; Daniel W. Mauney, Richmond, both of Va.

[73] Assignee: Virginia Polytechnic Institute & State University; Virginia Tech Intellectual Properties, Inc., both of Blacksburg, Center for Innovative Technology, Herndon, all of Va.

[21] Appl. No.: 569,812

[22] Filed: Aug. 20, 1990

[51] Int. Cl.$^5$ ............................................. A61F 11/00
[52] U.S. Cl. ..................................... 128/864; 128/865
[58] Field of Search .............................. 128/864–868; 264/466, 222

[56] References Cited

U.S. PATENT DOCUMENTS

| | | | |
|---|---|---|---|
| 3,097,059 | 7/1963 | Hoffman | 128/864 |
| 3,696,090 | 10/1972 | Lampe | 128/864 |
| 3,782,379 | 1/1974 | Lampe | 128/864 |
| 3,811,437 | 5/1974 | Gardner, Jr. | 128/864 |
| 3,833,701 | 9/1974 | Johnson | 128/864 |
| 3,872,559 | 3/1975 | Leight | 128/867 |
| 3,897,376 | 7/1975 | Lampe | 128/864 |
| 3,925,277 | 12/1975 | Lampe | 128/864 |
| 3,959,200 | 5/1976 | Scott | 523/121 |
| 4,160,449 | 7/1979 | Wade | 128/864 |
| 4,253,452 | 3/1981 | Powers | 128/864 |
| 4,372,904 | 2/1983 | Gunn | 264/130 |
| 4,434,794 | 3/1984 | Leight | 128/867 |
| 4,459,247 | 7/1984 | Rothemund | 128/864 |
| 4,579,112 | 4/1986 | Scott | 128/864 |
| 4,608,217 | 8/1986 | Csiki | 128/864 |
| 4,774,938 | 10/1988 | Leight | 128/864 |
| 4,828,325 | 5/1989 | Brooks | 264/222 |
| 4,871,502 | 10/1989 | LeBish | 264/222 |

FOREIGN PATENT DOCUMENTS

| | | |
|---|---|---|
| 0183171 | 9/1955 | Fed. Rep. of Germany ...... 128/864 |
| 1559694 | 12/1967 | France . |
| 2090535 | 1/1982 | United Kingdom . |
| 2084072 | 4/1982 | United Kingdom . |

OTHER PUBLICATIONS

Berger, E. H. (1986), Hearing protection devices. in E. H. Berger, W. D. Ward, J. C. Morrill, and L. H. Royster (Eds), Noise and hearing conservation manual (pp. 319–381), Akron, OH: American Industrial Hygiene Association.
Smith, K. E. (1977), Earmolds and hearing aid accessories, In W. R. Hodgson and P. H. Skinner (Eds.), Hearing aid assessment and use in audiologic habilitation (pp. 42–66), Baltimore: Williams & Wilkins.
Gasaway, D. C. (1985), Hearing conservation: A practical manual and guide, Englewood Cliffs, N.J.: Prentice-Hall, Inc.
Nixon, C. W. (1972), Hearing protective devices: Ear protectors, in C. M. Harris (Ed.), Handbook of noise control (pp. 12.1–12.13), New York: McGraw-Hill Book Company.

Primary Examiner—Robert A. Hafer
Assistant Examiner—Michael Brown
Attorney, Agent, or Firm—Whitham & Marhoefer

[57] ABSTRACT

A custom-fitting earplug (18) for hearing protection or other ear applications, or in-ear communications device mounting (40) is fabricated in situ by depositing a foaming material (14 or 24) within the person's ear (10 or 42, respectively) and allowing the foaming material (14 or 24) to expand therein to form foam (16 or 44, respectively). By applying slight pressure from outside the person's ear (10 or 42) through the stem (13) and/or keeper (11) during expansion, the foam (16 or 44, respectively) will be tightly packed in and conform to the ear canal. An optional sheath (15 or 36) positioned over the foaming material (14 or 24, respectively) serves to provide a smooth outer surface for the earplug (18) or communications device (40) produced and can aid in defining and limiting the expansion of the foam (14 or 24, respectively).

11 Claims, 2 Drawing Sheets

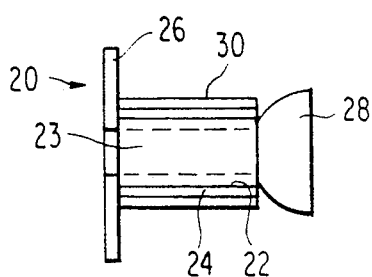
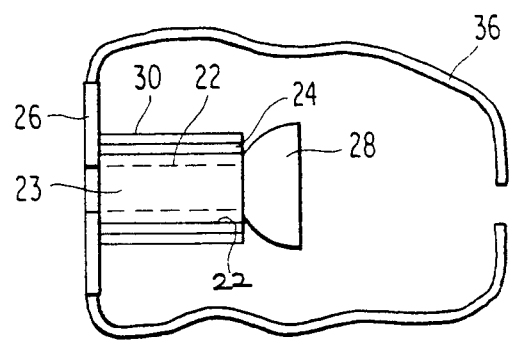
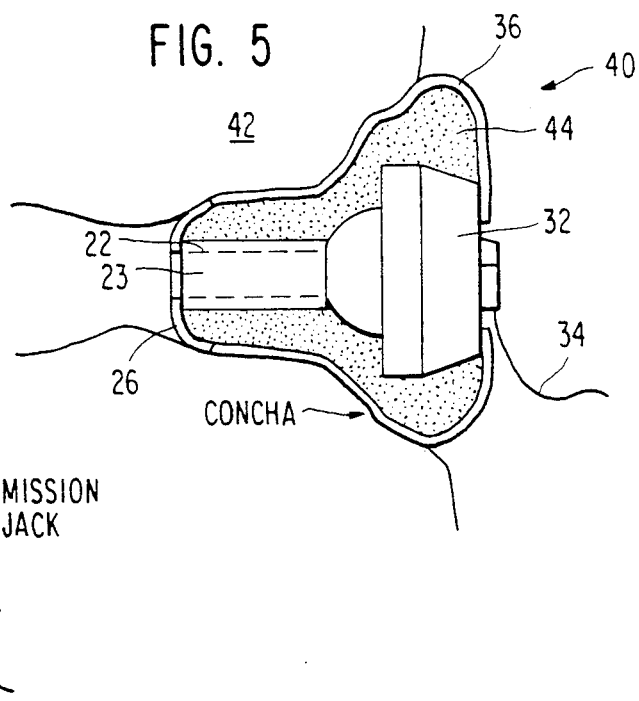

CUSTOM-FITTING EARPLUG FORMED IN SITU USING FOAMING ACTION

BACKGROUND OF THE INVENTION

1. Field of the Invention

The present invention generally relates to custom-fitting earplugs that are formed in situ and, more particularly, to a device and method for creating a custom-fitting earplug in the ear of the prospective user which utilizes a foaming agent that expands and fills the ear canal after its insertion in the patient's ear. These earplugs have multiple applications as hearing protectors in noise, couplers for mounting electronic devices (e.g., hearing aids and communications transceivers) in the ear, ear canal measurement devices, and as ear seals for swimming and sleeping.

2. Description of the Prior Art

Earplugs are presently in common use in a number of activities. Airport and heavy industry personnel typically use noise-attenuating earplugs on a daily basis to prevent hearing damage. The Occupational Health and Safety Administration (OSHA) presently requires that all workers exposed to noise of 85 decibels A-weighted (dBA) time-weighted average over an eight hour day must be supplied with hearing protectors. According to recent estimates of the Environmental Protection Administration (EPA), over nine million American workers are exposed to levels above the threshold levels set by OSHA on a daily basis. In addition to industry, people often use earplugs when operating light machinery such as chain saws, when participating in sporting activities such as swimming and shooting, and when attending various spectator events such as automobile races and rock concerts.

Prior art "universal fit" type earplugs typically comprise a foam, mineral fiber, wax, or putty-like (e.g., Swedish Wool) material which is either unencapsulated or sheathed in a thin, smooth outer skin. Outside the wearer's ear the plugs may have a cylindrical or other pre-formed shape. These plugs are often termed "universal fit" because they are intended to adapt to the contours of any person's ear canal to provide hearing protection. To install the "universal fit" earplug, the wearer must first compress and/or form the plug by kneading, wadding or rolling it up and then position the plug in his or her ear canal. In the case of the foam earplug, the plug must be inserted before it expands. After insertion, the "universal fit" plug is supposed to assume the natural contours of the ear canal by expansion therein. Typical examples of "universal fit" foam earplugs are shown and discussed in U.S. Pat. No. 4,160,449 to Wade, U.S. Pat. No. 4,459,247 to Rothemund, and U.S. Pat. No. 4,434,794 to Leight.

Universal fit earplugs suffer from a variety of problems. First, the plugs are difficult for many individuals to insert properly. If the plug is incorrectly formed by the user as it is inserted in the ear canal, wrinkles and voids may develop that allow sound leakage to the user's eardrum, thereby reducing the protective effectiveness of the plugs to the wearer. Second, some of the plugs typically are larger than some people need because the commercial vendor has designed the plugs to fit ear canals that are larger than average in hopes of accommodating a wide range of users. Third, some users find universal fit earplugs to be uncomfortable.

Custom-molded earplugs can be an attractive alternative to universal fit earplugs and have advantages in their comfort, more reliable fit, and lower long-term costs due to longer usable life. Also, custom-molded earplugs may offer certain hygiene advantages in dirty environments since the user does not have to compress or form them with their fingers prior to insertion. Custom-molded earplugs are essentially a mold of the wearer's ear canal and concha of the outer ear. Hence, the earplugs can be precisely positioned in the ear by the wearer so that his or her ear canal is not subjected to undue pressure when the plugs are installed and because of the personalized fit, sound is effectively blocked by the plugs. Some custom-molded earplugs are made by making a positive casting of the ear canal first, then making a negative mold, and finally making the earplug from the negative mold.

U.S. Pat. No. 3,097,059 to Hoffman discloses a method of making earplugs in situ which eliminates the need for making negative and positive casts. The earplug is fabricated by depositing a mass of acrylic resin in the wearer's ear and allowing the acrylic to cure therein. U.S. Pat. Nos. 3,696,090, 3,782,379, 3,897,376, and 3,925,277 to Lampe disclose two part room temperature vulcanizable rubber compositions which are used to form earplugs in situ in a manner similar to that described in Hoffman.

Casting an earplug in situ using a self-curing resin is not an ideal method for creating a custom-molded earplug. A doctor or a trained technician will be required to make the mold since the mold's manufacture requires a highly viscous resin or putty to be deposited deep in the patient's ear. The objective when taking the earmold is to obtain an impression which follows all inner contours of the ear canal and which has no voids or creases due to the trapped air pockets. Packing the resin in the ear canal to meet this objective can be very painful to the patient. During packing, air is trapped between the tympanic membrane (eardrum) and the viscous resin. Because of the viscosity of the resin, air cannot easily escape the ear canal through or around the resin; therefore, external pressures exerted to pack the resin in the ear will be transferred to the tympanic membrane and to middle ear structures. The viscous resin can be forced into the ear canal using a large syringe. Alternatively, a paste-like resin material can be inserted into the ear canal using a putty knife or the doctor's thumb to force the resin down into the ear canal. After the resin is added to the ear, it may be necessary to manually apply some pressure from outside the ear to assure that the resin hardens within the canal. The patient must sit motionless, without jaw movement, for several minutes until the mold solidifies.

Besides severe pain being caused to many patients, casting an earplug in situ also suffers from the common problem of voids being formed therein which reduce the effectiveness of the final earplug produced. This results in the need for taking multiple impressions. For example, if the resin is not packed into the user's ear tightly enough, air pockets will be created in spaces where the resin does not contact the walls of the ear canal or invisible voids may occur within the resin structure itself. British Patent 2,084,072 to Carr addresses this problem by providing additional coatings on the outside surface of the plug until a perfect impression is made. Such a tedious process for forming an earplug is believed not to be acceptable.

British Patent 2,090,535 to Fekry discloses an improved method for creating an earplug in situ. A water swellable insert is first installed in the ear, then water drops are added to the insert causing it to expand inside the ear to a preset shape. While the insert described in the patent may avoid the disadvantage of pain to the wearer of custom-molding earplugs (assuming the preset size does not exert pressure on the ear canal walls), it does not create a custom-fitting earplug in its expanded state. Rather, the insert expands to one preset shape and would suffer from the same disadvantages discussed above in conjunction with universal fit type earplugs.

SUMMARY OF THE INVENTION

It is therefore an object of the present invention to provide an earplug device which can form a custom-fitting earplug in situ with a minimum of pain and discomfort to the patient.

It is another object of the invention to provide an earplug device which can form a custom-fitting earplug in situ without complex molding operations and without requiring special medical or audiological skills.

It is another object of the invention to enable production of a custom-fit earplug which is immediately usable and does not require positive casts and negative molds nor waiting on the part of the patient in situ.

It is still another object of the invention to provide a device which can house a custom-fitting hearing aid or communications transceiver in situ.

It is an additional object of this invention to provide a means of obtaining anthropometric ear canal measurements.

It is a further object of this invention to provide a custom-fitting earplug and ear coupler which can act as a hearing protector to guard against high noise environments.

According to the invention, a foaming material is positioned within the ear canal of the prospective wearer and is used to create a custom-fitting earplug. The foaming material, in its unexpanded state, is small in size and may be, though not necessarily, surrounded by a thin plastic or membrane material which constitutes a sheath. This device comprises a core approximately 0.5-2.5 cm long coated with a foaming material which is protected by a removable wrapping and terminated by a protective flange. Further, the device includes a removable keeper, stem, and an optional inserter to aid in the donning and doffing of the device. After the device has been placed in the ear, the foaming material expands to create a foam which fills the ear canal and part of the concha. Preferably, ambient conditions within the ear, such as heat and humidity, trigger the foaming action. Other external agents, such as water or chemical products can also be used to induce foaming on demand. During foaming, the wearer should apply only slight fingertip pressure to the earplug so that the foaming action does not push the device out of the ear. After the foam has formed and is set, the earplug can be removed and re-installed whenever the wearer desires. The sheath provides a smooth, cleanable exterior surface for the earplug which has been created in situ, as well as defines and limits the area into which the foam can expand.

In a further embodiment of the invention, a device containing the foaming material is used to create an ear coupler mounting for a custom-fitting hearing aid or similar device. The device comprises a small diameter (approximately 1-3 mm) cylindrical body member of approximately 0.5-2.5 cm having a hollow passage therethrough. A protective flange and a mounting flange are positioned on opposite ends of the body member. The mounting flange is positioned above the hollow passage in the cylindrical body member and is modifiable to secure ear microphones, communications transceivers, or other electronic equipment. Carried on the outside surface of the cylindrical body member is a foaming material. The foaming material can be kept in a stable, non-reactive state by applying a tape material over top. A membrane sheath can be secured to the protective flange of the cylindrical body and extend over the outside of the entire device. To create a custom-fitting hearing aid or ear microphone, packaged electronics are connected to the mounting flange of the device, the tape is removed from over top the foaming material, and the combined device is placed in the patient's ear canal. The foaming material is then induced to expand to fill the spaces between the cylindrical body member and the ear canal with a foam material. After the foam has formed and set, the hearing aid or ear microphone can be removed and re-installed in the patient's ear whenever desired. The hollow passage in the cylindrical body allows auditory communication directly between the patient's eardrum and the hearing aid or ear microphone.

BRIEF DESCRIPTION OF THE DRAWINGS

The foregoing and other objects, aspects and advantages will be better understood from the following detailed description of a preferred embodiment of the invention with reference to the drawings, in which:

FIG. 2 is a cross-sectional side view of a package used in creating a custom-fitting hearing aid;

FIG. 3 is a cross-sectional side view of the package shown in FIG. 2 where a sheath material has been connected to the rear protective flange of the package;

FIG. 4 is a representational side view of a ear microphone and transmission wire; and FIG. 5 is a cross-sectional side view of a custom-fitting ear microphone created from the device shown in FIG. 3.

DETAILED DESCRIPTION OF A PREFERRED EMBODIMENT OF THE INVENTION

Figure 1A:
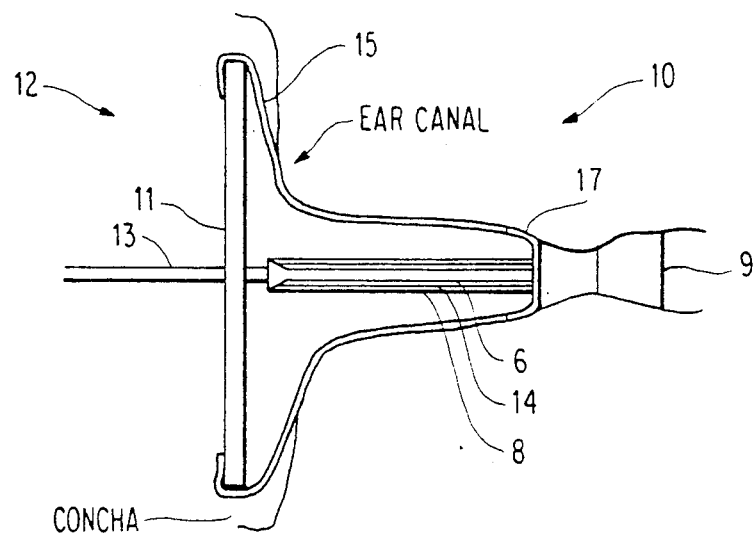
FIGS. 1a and 1b are cross-sectional side views of a person's ear canal before and after creation of a custom-fitting earplug, respectively.
Figure 1B:
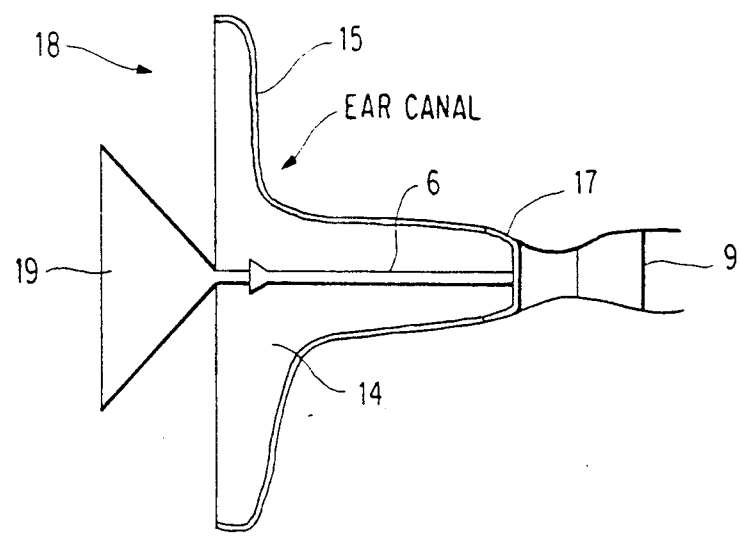

Referring now to the drawings, and more particularly to FIGS. 1a and 1b, there is shown generally the ear 10 of a person with a package 12 positioned within the person's ear canal. The package 12 contains a foaming material 14 coated on a core 6 and an outer sheath 15. The foaming material 14 is preferably chosen to expand to form a foam 16 under the ambient conditions present within the ear 10, such as body temperature and humidity; however, it is anticipated that other triggering mechanisms, such as adding a chemical, exposure to ultraviolet light, water, or any other convenient treatment of the foaming material 14 could be used to activate the foaming material 14 just prior to insertion in the ear 10. Selection of the foaming material 14 may obviously control the type of triggering mechanism used. In addition, the quantity of foaming material 14 used will be dependent on type of foam 16 and the anthropometry of the ear canal and should be selected so that the foam 16 will slightly overfill the volume in the ear canal and slightly protrude out into the concha of the ear 10. It is also preferred that the foaming material 14 and foam 16 created during expansion be non-inflammatory, dielectric, and retain its final expanded shape and size conforming to the ear canal walls. The foam 16 should also act as a barrier by reflecting and by attenuating sound, and have a high transmission loss. To achieve a high transmission loss, the foam 16 should generally have a high flow resistance, a high density, and a moderately low bulk modulus.

In operation, a person places the package 12 in his or her ear 10 using stem 13 and keeper 11 and because of the ambient conditions therein or due to other triggering agents applied just prior to insertion, the foaming material 14 expands to fill the ear canal with foam 16. A removable wrapping 8 can be used to protect the foaming material 14 prior to insertion and then removed upon insertion. The stem 13 aids insertion by providing an area for the forefinger and thumb to grasp and guide package 12 into the canal. The keeper 11 prevents insertion of the device too far into the ear canal as well as to guide the overflowing foam into the contours of the concha. The stem 13 and keeper 11 are not necessarily present during the wearing of the earplug. Preferably, the stem 13 and keeper 11 can be easily removed from the earplug through a twisting motion once the foaming has taken place. The twisting motion can serve to detach the stem 13 from a fitting connecting it to the core 6 or it could serve to physically break off the stem 13 at a weakened section. The optional inserter 19 can then be affixed to the earplug through a twisting motion and serve to aid in the donning and doffing of the device under normal operating conditions.

An "eardam" 9, made of a cotton or mineral fiber swab attached to a thread extending out of the ear, may be optionally inserted ahead of the package 12, to ensure that the foam 16 does not reach the eardrum. However, the built-in protective flange 17 on the insertion end of the package is intended for this purpose and may render eardams unnecessary. Preferably, the protective flange 17 is a soft, flexible polymer material which bends backwards into a hemispherical shape when inserted so as to prevent undue irritation to the ear canal and to limit the forward (toward eardrum) expansion of the foam 16. The protective flange 17 should be no more than 15 mm in diameter.

In order to keep the package 12 within the ear 10 during foaming, the person simply holds his or her thumb and/or forefinger against the stem 13 or keeper 11. After the foam 16 has set, a custom-fitting earplug 18 will have been created. The earplug 18 can then be removed and re-installed in the ear 16 whenever desired. The earplug 18 retains its shape upon removal from the ear 10. The optional outer sheath 15 of the package 12 gives a smooth, cleanable surface to the earplug 18 produced. The sheath 15, in conjunction with the protective flange 17, can serve to distance the person's eardrum (not shown) from the foam 16. Hence, the need for installing an eardam in the ear 10 before creating the earplug 18 is eliminated.

A particular advantage of the above device and method of making earplugs in situ is that the earplug 18 is created and used with relatively little pain and discomfort to the person. The ear canal is merely subjected to the expansion pressure of the foam 16 as it expands, and this is controllable through foam selection. Because the device and method of making earplugs is relatively rapid and painless and fills the wearer's ear canal, the device could be used as a tool for measuring and determining the shape of the wearer's ear canal. After making the earplug 18, it can be extracted and any portion can be quickly measured with available measuring gauges. Hence, population data on the anthropometry of ear canals can be rapidly gathered. Prior art anthropometric data has been achieved through the tedious and relatively imprecise process of inserting spherical balls of fixed sizes in the patient's ear.

FIGS. 2-5 disclose a further embodiment of this invention wherein a custom-fitting hearing aid or ear microphone can be created in situ. FIG. 2 shows a device 20 comprised of a cylindrical body 22 having a foaming material 24 carried on its outer surface. The cylindrical body 22 has a central bore 23 therethrough and includes a protective flange 26 on one end and a mounting flange 28 on its other end. The cylindrical body 22, protective flange 26, and mounting flange 28 could be integrally molded or could be assembled from three separate pieces. The protective flange 26 can serve to protect the person's eardrum (not shown) from the foam 16. The protective flange 26 would serve the same purposes described above in conjunction with FIGS. 1a and 1b. The mounting flange 28 should be sturdy and rigid enough to support a packaged electronic component (shown in FIG. 4 as item 32) and serves to join the component to the cylindrical body 22 at the central bore 23 so that airborne sound waves pass relatively unobstructed therethrough to the person's eardrum. The packaged electronic component 32 can be a communications transceiver such as those sold by Maxon ®, an ear microphone such as the AICOMM AIMic ™, a hearing aid, or any other desired component. The electronic component 32 may or may not have a transmission wire 34 which can be disconnected. A removable wrapping 30 can be positioned over the foaming material 24 so that it is protected from the elements prior to use. FIG. 3 shows that an optional sheath 36 can be affixed to the protective flange 26. The sheath 36 would serve the same purposes described above in conjunction with FIGS. 1a and 1b.

As shown in FIG. 5, a custom-fitting hearing aid or ear microphone mount 32 is fabricated in situ in the person's ear 42. The foaming material 24 (shown in FIGS. 3 and 4) expands to fill the ear canal with a foam 44 as described above. After the foam 44 has set, the custom-fitting hearing aid or ear microphone can freely be removed from and re-installed in the ear 42. The custom-fitting hearing aid or ear microphone retains its shape when removed from the ear. The electronic component 32 is in direct audible communication with the eardrum through central bore 23.

While the invention has been described in terms of its preferred embodiments which include a foaming material used to create a custom-fitting earplug or ear microphone in situ, those skilled in the art will recognize that the invention can be practiced with modification within the spirit and scope of the appended claims.

Having thus described our invention, what we claim as new and desire to secure by Letters Patent is as follows:

1. An earplug device comprising:
   a body member positionable within an ear canal of a person; and
   a foaming material in a non-foamed state carried by said body member, said foaming material having a means for foaming in said ear canal in order to fill said ear canal with foam which retains the shape of said ear canal upon removal, said body member includes a core on which said foaming material is carried, a stem extending from said core, and a keeper connected to said stem, said keeper preventing said body member from being inserted too far into said ear canal and for guiding expanding foaming material.

2. An earplug device as recited in claim 1 wherein said stem is weakened such that said stem and keeper can be removed from said core after said foaming material expands to form said foam.

3. An earplug device as recited in claim 1 wherein said stem is disconnectably attached to said core by a fitting, said stem being disconnectable from said fitting after said foaming material expands to form said foam.

4. An earplug device comprising:
   a body member positionable within an ear canal of a person;
   a foaming material in a non-foamed state carried by said body member, said foaming material having a means for foaming in said ear canal in order to fill said ear canal with foam which retains the shape of said ear canal upon removal; and
   a removable wrapping material positioned over said foaming material for preventing the expansion of said foaming material before insertion into said ear canal.

5. An earplug device comprising:
   a body member positionable within an ear canal of a person, said body member having a hollow passage therethrough and a means for mounting an electronic device thereon; and
   a foaming material in a non-foamed state carried by said body member, said foaming material having a means for foaming in said ear canal in order to fill said ear canal with foam which retains the shape of said ear canal upon removal.

6. A method of collecting population anthropometric data on the size and shape of the human ear canal, comprising the steps of:
   placing a foaming material within an ear canal of each person within a test group and allowing said foaming material to expand so as to create a foam which fills said ear canal, said foam capable of retaining its shape upon removal from said ear canal;
   measuring the dimensions and determining the shape of said foam after removal from said ear canal; and
   recording the measured dimensions and shape of said foam for each of said persons in said test group.

7. An earplug device comprising:
   a body member positionable within an ear canal of a person, said body member having first and second ends;
   a foaming material in a non-foamed state carried by said body member, said foaming material having a means for foaming in said ear canal in order to fill said ear canal with foam which retains the shape of said ear canal upon removal, said body member including a core on which said foaming material is carried; and
   a sheath connected to said body member at or near said first end and extending radially therefrom towards said second end of said core, said sheath being positioned over said foaming material in said non-foamed state.

8. An earplug device as recited in claim 7 wherein said sheath provides an outer layer to foam formed from said foaming material in said non-foamed state.

9. An earplug device as recited in claim 7 wherein said sheath is connected to said first end of said body member by a protective flange which projects radially from said first end of said core.

10. An earplug device as recited in claim 7 wherein said means for foaming said foaming material in said non-foamed state comprises chemical constituents selected from the group consisting of constituents that are activatable by ambient conditions in an ear and constituents that are activatable by an external means.

11. An earplug device comprising:
   a body member positionable within an ear canal of a person, said body member having first and second ends;
   a foaming material in a non-foamed state carried by said body member, said foaming material having a means for foaming in said ear canal in order to fill said ear canal with foam which retains the shape of said ear canal upon removal;
   a flange radially projecting from a first end of said body member.

* * * * *